US00PP15840P2

(12) United States Plant Patent
Jonkers

(10) Patent No.: US PP15,840 P2
(45) Date of Patent: Jul. 5, 2005

(54) **DOUBLE *IMPATIENS* PLANT NAMED 'DIDI ORANGE TWO'**

(50) Latin Name: *Impatiens walleriana*
Varietal Denomination: Didi Orange Two

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,350

(22) Filed: Apr. 5, 2004

(51) Int. Cl.[7] ..... A01H 5/00
(52) U.S. Cl. ..... Plt./317
(58) Field of Search ..... Plt./317

(56) References Cited

U.S. PATENT DOCUMENTS

PP12,430 P2 * 2/2002 Heffner ..... Plt./317
PP13,643 P2 * 3/2003 Uchneat ..... Plt./317
PP13,663 P2 * 3/2003 Uchneat ..... Plt./317
PP13,889 P2 * 6/2003 Sijm ..... Plt./317
PP14,604 P2 * 3/2004 Cascante ..... Plt./317

OTHER PUBLICATIONS

UPOV ROM GTITM Computer Database, GTI Jouve Retrieval Software 2004/04 Citation for 'Didi Orang Two'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of Double *Impatiens* plant named 'Didi Orange Two', characterized by its compact, upright, outwardly spreading and mounded plant habit; freely branching growth habit; dark green-colored leaves; freely flowering habit; and orange-colored flowers that are fully double and positioned above and beyond the foliage.

1 Drawing Sheet

Botanical designation: *Impatiens walleriana.*
Variety denomination: 'Didi Orange Two'.

BACKGROUND OF THE INVENTION

The present Invention relates to a new and distinct cultivar of Double *Impatiens* plant, botanically known as *Impatiens walleriana,* and hereinafter referred to by the name 'Didi Orange Two'.

The new Double *Impatiens* is a product of a planned breeding program conducted by the Inventor in Andijk, The Netherlands. The objective of the breeding program was to develop new compact Double *Impatiens* cultivars with fully double flowers, freely branching and flowering habit, early flowering and attractive flower and foliage coloration.

The new *Impatiens* originated from a cross-pollination made by the Inventor in March, 2000, of a proprietary *Impatiens walleriana* selection identified as code number IW-622-3, not patented, as the female, or seed parent, with a proprietary *Impatiens walleriana* selection identified as code number IN-1791-14, not patented, as the male, or pollen parent. The cultivar Didi Orange Two was discovered and selected by the Inventor as a flowering plant within the progeny of the stated cross-pollination in a controlled environment in Andijk, The Netherlands in September, 2000.

Asexual reproduction of the new cultivar by terminal cuttings taken in Andijk, The Netherlands since September, 2000, has shown that the unique features of this new *Impatiens* are stable and reproduced true to type in successive generations of asexual reproduction.

SUMMARY OF THE INVENTION

The following traits have been repeatedly observed and are determined to be the unique characteristics of 'Didi Orange Two'. These characteristics in combination distinguish 'Didi Orange Two' as a new and distinct Double *Impatiens* cultivar:

1. Compact, upright, outwardly spreading and mounded plant habit.
2. Freely branching growth habit.
3. Dark green-colored leaves.
4. Freely flowering habit.
5. Orange-colored flowers that are fully double and positioned above and beyond the foliage.

Plants of the new *Impatiens* differ primarily from plants of the female parent selection in the following characteristics:

1. Plants of the new *Impatiens* are more compact than plants of the female parent selection.
2. Leaves of plants of the new *Impatiens* are dark green in color whereas leaves of plants of the female parent selection are reddish green in color.
3. Plants of the new *Impatiens* and the female parent selection differ in flower color as plants of the female parent selection have red-colored flowers.

Plants of the new *Impatiens* differ primarily from plants of the male parent selection in the following characteristics:

1. Plants of the new *Impatiens* are more vigorous than plants of the male parent selection.
2. Plants of the new *Impatiens* have fully double flowers whereas plants of the male parent selection have semi-double flowers.
3. Plants of the new *Impatiens* and the male parent selection differ in flower color as plants of the male parent selection have scarlet red-colored flowers.

The new *Impatiens* can be compared to the *Impatiens walleriana* cultivar Balfiedeor, (U.S. Plant Pat. No. 13,643).

However, in side-by-side comparisons conducted in Gilroy, Calif., plants of the new *Impatiens* differed from plants of the cultivar Balfiedeor in the following characteristics:

1. Leaves of plants of the new *Impatiens* were darker green in color than leaves of plants of the cultivar Balfiedeor.
2. Flowers of plants of the new *Impatiens* were slightly lighter in color than flowers of plants of the cultivar Balfiedeor.
3. Sepals of plants of the new *Impatiens* were larger than sepals of plants of the cultivar Balfiedeor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens*.

The photograph at the top of the sheet comprises a side perspective view of a flowering plant of 'Didi Orange Two'.

The photograph at the bottom of the sheet is close-up view of typical flowers and leaves of 'Didi Orange Two'.

DETAILED BOTANICAL DESCRIPTION

Plants of the cultivar Didi Orange Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Rooted young plants were planted in containers and had been growing for about five months when the photographs and the description were taken. In the following description, color references are made to The Royal Horticultural Society Colour Chart, 1995 Edition, except where general terms of ordinary dictionary significance are used.

Botanical classification: *Impatiens walleriana* cultivar Didi Orange Two.

Parentage:

*Female parent.*—Proprietary *Impatiens walleriana* selection identified as code number IW-622-3, not patented.

*Male parent.*—Proprietary *Impatiens walleriana* selection identified as code number IN-1791-14, not patented.

Propagation:

*Type cutting.*—Terminal cuttings.

*Time to initiate roots.*—About 10 to 21 days at 22 to 23° C.

*Time to produce a rooted young plant.*—About 28 days at 16 to 24° C.

*Root description.*—Fine, fleshy; white in color.

*Rooting habit.*—Freely branching.

Plant description:

*General appearance.*—Compact, upright, outwardly spreading and mounded plant habit.

*Growth and branching habit.*—Vigorous and freely-branching growth habit with about eight basal branches; lateral branches potentially forming at every node; dense and bushy growth. Pinching enhances branching.

*Plant height.*—About 22 cm.

*Plant diameter or spread.*—About 52 cm.

*Lateral branches.*—Length: About 26 cm. Diameter: About 1 cm. Internode length: About 4.2 cm. Texture: Smooth, glabrous. Color: 146B with splotches of 185B.

*Foliage description.*—Arrangement: Alternate, simple. Length: About 7 cm. Width: About 4.7 cm. Shape: Elliptical. Apex: Acuminate. Base: Attenuate. Margin: Crenate with sparse ciliation. Texture, upper and lower surfaces: Smooth, glabrous. Venation pattern: Pinnate. Color: Developing foliage, upper surface: Darker than 147A. Developing foliage, lower surface: 147B overlaid with 184A. Fully expanded foliage, upper surface: Darker than 147A. Venation, upper and lower surfaces: 147B. Petiole: Length: About 2.3 cm. Diameter: About 3 mm. Texture, upper and lower surfaces: Smooth, glabrous. Color: 148B.

Flower description:

*Flower type and habit.*—Numerous and consistently double flowers. Flower buds open similar to a rose in fullness; flowers rounded in shape. Flowers arise from leaf axils. Freely flowering, usually about 30 flowers and flower buds per lateral branch. Flowers positioned above the foliage and typically face upright or outward. Flowers last about five to seven days under greenhouse conditions. Flowers not persistent. Flowers not fragrant.

*Natural flowering season.*—Flowering is continuous through the spring and summer.

*Flower size.*—Diameter: About 4.5 cm. Depth: About 2 cm.

*Flower buds* (*at stage of showing color*).—Length: About 1.7 cm. Diameter: About 1.2 cm. Shape: Ovoid. Color: 43D.

*Petals.*—Quantity/arrangement: About 46 per flower; imbricate. Length, outermost petals: About 2.3 cm. Width, outermost petals: About 2.5 cm. Length, innermost petals: About 5 mm. Width, innermost petals: About 7 mm. Shape: Obovate to cordate. Apex: Rounded and occasionally emarginate. Base: Acute. Margin: Entire. Texture, upper and lower surfaces: Smooth, glabrous. Color: When opening, upper surface: 44A. When opening, lower surface: 43B. Fully opened, upper surface: 43A. Fully opened, lower surface: 43B.

*Sepals.*—Quantity/arrangement: Five in a single whorl; one modified into an elongated spur. Calyx length: About 1 cm. Calyx diameter: About 1 cm. Shape: Elliptic. Apex: Acute. Margin: Entire. Texture, upper and lower surfaces: Smooth, glabrous. Color, upper and lower surfaces: Close to 144A. Spur length: About 3.8 cm. Spur diameter: At flower, about 2 mm; at apex, less than 1 mm. Spur color: 177C.

*Peduncles.*—Length: About 2.6 cm. Diameter: About 2 mm. Angle: About 45° from vertical. Strength: Strong. Texture: Smooth, glabrous. Color: 146C.

*Reproductive organs.*—None observed.

*Seed/fruit.*—None observed.

Disease/pest resistance: Plants of the new *Impatiens* have not been observed to be resistant to pathogens and pests common to *Impatiens*.

It is claimed:

1. A new and distinct cultivar of Double *Impatiens* plant named 'Didi Orange Two', as illustrated and described.

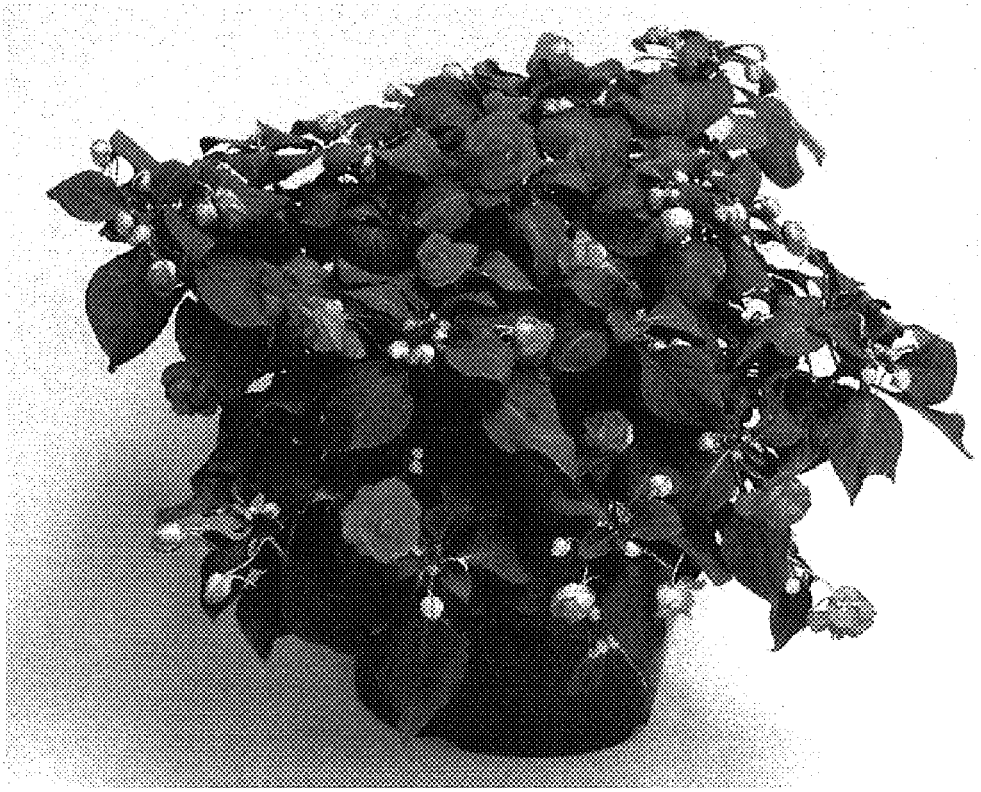
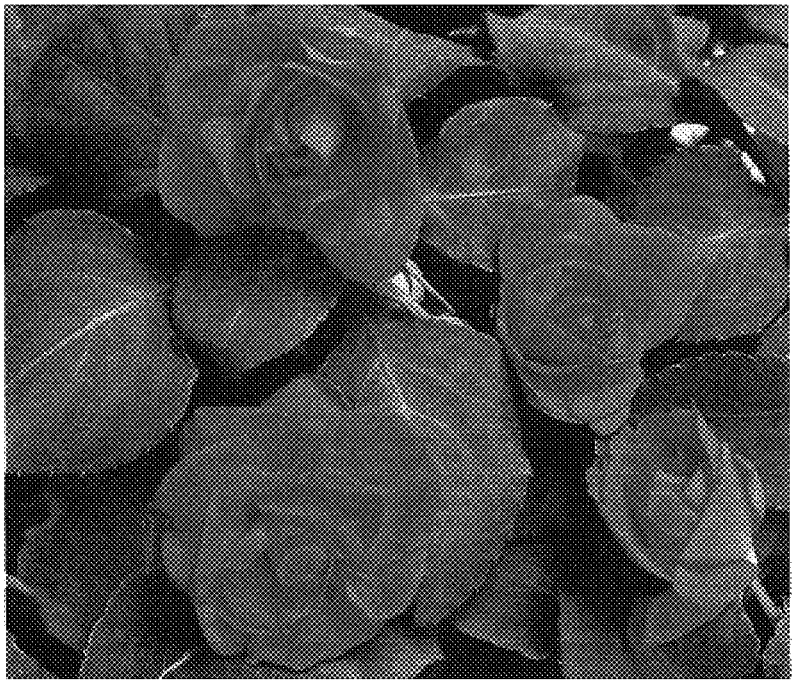

* * * * *